United States Patent

Becker et al.

[11] 4,130,433
[45] Dec. 19, 1978

[54] INDUSTRIAL BIOCIDES

[75] Inventors: Frank C. Becker, Gurnee; Jorge P. Li, Libertyville, both of Ill.

[73] Assignee: Abbott Laboratories, North Chicago, Ill.

[21] Appl. No.: 805,243

[22] Filed: Jun. 10, 1977

[51] Int. Cl.$^2$ ................................................ C09D 5/14
[52] U.S. Cl. ........................... 106/15 R; 260/45.8 N; 260/326.5 FM; 264/194; 424/274
[58] Field of Search ............... 260/326.5 FM, 45.8 N; 106/15 R, 176; 424/274; 264/194

[56] References Cited

U.S. PATENT DOCUMENTS 3,821,247  6/1974  Sturm et al. ............... 260/326.5 FM

FOREIGN PATENT DOCUMENTS 1346586  2/1974  United Kingdom .......... 260/326.5 FM Primary Examiner—Lorenzo B. Hayes
Attorney, Agent, or Firm—Paul D. Burgauer; Robert L. Niblack

[57] ABSTRACT

N-Phenoxyphenyl or N-phenylthiophenyl maleimides or 2,3-dichloromaleimides carrying optional substituents in the phenyl rings are potent biocides capable of protecting fabrics and plastics from fungal or bacterial attacks.

15 Claims, No Drawings

INDUSTRIAL BIOCIDES

DETAILED DESCRIPTION OF THE DISCLOSURE

Synthetic, film-forming materials, such as those used in the manufacture of plastic films and woven fabrics made from synthetic or cellulosic fibers are known to be subject to bacterial or fungal attacks. This is particularly known to those manufacturers whose products will be used on exterior surfaces and/or under conditions that are prone to host undesirable fungal and bacterial micro-organisms.

In order to prevent bacterial or fungal attack and consequent deterioration of the polymeric or cellulosic material so attacked or the substrate to which they are applied, manufacturers of plastic films or woven fabrics have used a number of biocides on a routine basis. Many of the currently used industrial biocides are organometallics, such as arsenicals; they are highly successful in preventing bacterial or fungal deterioration of plastics. For environmental reasons, however, organometallics are now less accepted in some of the industrial uses where biocides are needed. It has thus become highly desirable to find new, non-metallic biocides that provide protection for polymeric substrates of all types, including film-formers, plastics, cellulosics, and the like.

It has now been found that a cellulosic, plastic or film-forming polymeric composition, knitted, woven, molded or extruded into a continuous form can be protected against bacterial or fungal attacks by treating such substrates with the compounds of the current invention. strates with the compounds of the current invention. These compounds are represented by the formula

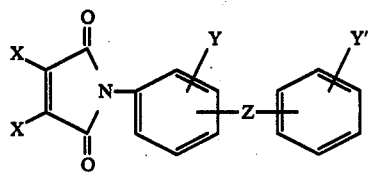

I wherein substituents X both are either hydrogen or chlorine, Y represents 0–1 and Y' represents 0–2 substituents taken from the group consisting of halogen, trifluoromethyl, alkoxy of 1–4 carbon atoms, carboxy, lower-alkoxycarbonyl, and nitro, and Z is O or S, with the proviso that when Z is O, at least one substituent Y or Y' must be present. These compounds are potent biocides; they can easily be incorporated into or applied to the surface of plastics, polymers, cellulosics and similar organic substrates. At concentrations of 0.005–5.0% by weight, the new compounds will completely protect said substrates against bacteria or fungi often found in the environment.

When a substrate is treated with the compound of formula I, growth of bacteria or fungi also is often inhibited in areas in contact with the surface of said treated substrate, particularly when said compound is present in the higher range of the concentration recited above.

For the purpose of the present description, the term "film-forming" should be understood to refer to the polymeric particles, whether those particles are present as dry, particulate matter or in liquid, dissolved, suspended, coherent, continuous or any other form, particularly including the ultimate form for which said particles are designed. The term "plastic" is used in a similarly broad version and is to be undertood to include those polymeric materials which can be extruded, injection- or compression-molded into the desired ultimate shape. The term "cellulosic" is primarily designed to refer to cotton, but also includes those cellulosic derivatives wherein the basic cellulosic structure of the fibrous material has undergone some chemical modifications that do not materially change the number of repeating units in the cellulose structure.

The current biocides are particularly useful for the treatment of leather, leather substitutes, wood or plastic products, or fabrics made from cellulosic or olefin polymers, knitted, woven, extruded or molded into structures exposed to outdoor conditions, such as outdoorwear, tents, boots, belts, tarpaulins, swimming pool liners and the like. The new biocides can similarly usefully be employed as additives to industrial fluids, e.g., cooling water, hydrocarbon fluids, cutting fluid; they also can be incorporated for their biocidal effect into cosmetics and, of course, paints of all types, including alkyd, oil-based or latex paints.

In a general embodiment, the compounds of the current invention are made by heating to reflux temperature for 1–5 hrs. an amine of the formula

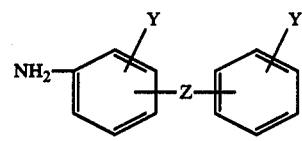

II wherein Y, Y' and Z have the same meaning as above with at least an equimolar amount of maleic or dichloromaleic anhydride in the presence of glacial acetic acid. In the cases where the product crystallizes out upon cooling, the crystalline product is collected by filtration, washed with ethanol and petroleum ether, and dried at 50° C. in vacuo. In the cases where no crystalline product separates upon cooling, acetic acid is removed from the reaction solution by vacuum-distillation or evaporating in vacuo. The residue is then triturated with dilute alcohol or water to give the product as a crystalline solid. The solid product is collected by filtration, washed with dilute alcohol or water, and dried at 50° C. over $P_2O_5$ in vacuo.

Normally, the product obtained in the above manner is quite pure. If further purification is desired, the above material can readily be purified either by recrystallization from an appropriate solvent or by column chromatography. For recrystallization, the following solvents or combination thereof are most suitable: lower alcohols, particularly methanol, ethanol, 2-propanol, aqueous alcohol, ethyl acetate, acetic acid, methylene chloride, chloroform, petroleum ether, benzene, toluene, acetone, dimethylformamide, dimethylsulfoxide. For column chromatography, both silica gel and neutral aluminum oxide can be used with excellent results. The best solvents or solvent combinations for elution where chloroform, methylene chloride, ethyl acetate, benzene, toluene, and petroleum ether.

The effect of the above new biocides is best understood by reference to a general embodiment: To a film-forming mixture containing a synthetic polymeric material which is to be processed into a continuous phase and contains the usual ingredients, such as dyes, pigments, plasticizers, preservatives and the like, is added between 0.005 and 5.0% by weight of the compound of formula I and all ingredients are dispersed to form a homogeneous mass. Such a mixture is stable under normal storage conditions; it can be stored for extended periods of time under conditions usually required for such materials. The shaped article made from or coated with this mixture is then resistant to fungal or bacterial attack. This is the case whether said article is obtained by compression-molding, injection-molding, extrusion or whether it is a surface film as obtained by aplying a coating formulation through brushing, spray-coating or dip-coating onto the substrate and subsequent drying. These coating methods primarily are applicable where the continuous substrate is a woven or knitted cellulosic material or wood. In most instances, the substrate and areas in contact therewith are also protectd from deterioration by bacterial or fungal attack.

In order to illustrate the effect of the addition of the compound of formula I to a film-forming or plastc mixture or a woven fabric, reference is made to the following examples which, however, are not intended to limit the invention in any respect.

EXAMPLE 1

A mixture of 11.5 g of p-phenylthioaniline and 9.5 g of dichloromaleic anyhdride in 50 ml of glacial acetic acid is heated at reflux for 3 hrs. Upon subsequent cooling, N-(p-phenylthiophenyl)-2,3-dichloromaleimide crystallized and is collected by filtration. The material is washed with ethanol and vacuum dried over $P_2O_5$, producing 15 g (75% of theory) of an analytical sample as a golden powder, melting at 151.5–153° C.

By substituting the above p-phenylthioaniline with o-phenylthioaniline, m-phenylthioaniline, or various chloro-, nitro-, trifluoromethyl, alkoxy-, alkoxy-carbonyl or carboxy substituted phenoxy- or phenylthioanilines, the above reaction produces similar yields of other new compounds identified in Structure I (X = Cl). By substituting the above dichloromaleic anhydride with an equimolar amount of maleic anhydride, the compounds of formula I (X = H) are obtained. Some of these compounds are listed in Table I together with some of their characteristics; many of their closely related analogs, i.e., those carrying one or more OMe, OBu or $CF_3$ substituents in place of Y or Y', show MIC data comparable to the data listed for the corresponding halogen derivatives.

EXAMPLE 2

In a minimum inhibitory concentration (MIC) test, the amount of the test compound needed to prevent fungal growth is established. In this test, agar containing the test compound at a specified concentration is inoculated with 1 ml of a broth containing 10,000 units each of *A.niger* and *P.funiculosum*. The agar plates inoculated in this fashion are incubated at 30° C. for 2 weeks and growth of the micro-organisms is determined by visual inspection to establish presence or absence of fungal growth.

The compounds made according to Example 1 and their MIC data are shown in the following table, wherein X, Y, Y' and Z are as indicated in Structure I.

Table I

| X | Y | Y' | Z | M.P. in ° C | MIC |
|---|---|---|---|---|---|
| H | H | 2,4-Cl$_2$ | O | 128–9 | 50–100 |
| H | 2-CO$_2$Me | 2,4-Cl$_2$ | O | bp.155–60, 0.003mm | 10–50 |
| H | H | H | S | 116–7 | 100–200 |
| H | H | 4-NO$_2$ | S | 181.5–2.5 | 50–100 |

Table I-continued

| X | Y | Y' | Z | M.P. in ° C | MIC |
|---|---|---|---|---|---|
| Cl | H | 2,4-Cl$_2$ | O | 155–6 | 1000–1500 |
| Cl | 3-Cl | 3,4-Cl$_2$ | O | 145–7 | >2000 |
| Cl | 2-CO$_2$Me | 2,4-Cl$_2$ | O | bp.190–5, 0.003mm | 1000–1500 |
| Cl | H | H | S | 151.5–53 | 500–1000 |
| Cl | H | 4-NO$_2$ | S | 185–6 | 50–100 |

In tests wherein cotton fabric samples are dip-coated in an aqueous solution containing compound I in such a manner that they contain 0.5% by weight of the latter, incubating said samples in nutrient agar for 24 hrs. at 37°0 C. with bacteria or mixed spores (*A.niger, A.flavus, C.globosum* and *P.funiculosum*) for 14 days at 28° C. it is shown that excellent protection is obtained. In many instances of compounds of Structure I, excellent protection is also obtained in areas surrounding and directly in contact with the cotton fabrics; also, in many instances, the same excellent results are obtained after leaching the samples for 24 hrs. in water or after exposing the samples for 24 hrs. to UV-light.

Similarly, the compounds of Structure I also prove to protect fabrics treated with 0.2 to 1% by weight after an accelerated humidity/heat test wherein the fabric samples are sandwiched between layers of loosely packed soil and kept for 14 days at 30° C. and 90% relative humidity.

Film formulations made from polyvinylchloride, containing the usual plasticizer, color stabilizer, preservative, UV stabilizer and 0.5% by weight of I, exposed up to 300 hrs. in a Weather-Ometer with intermittent water spray and subsequent inoculation with some of the bacteria or mixed spores mentioned above, show equal or better micro-organism resistance than those shown by commercially available biocides.

While the above examples are directed only to some of the p-phenyl substituted ethers or thioethers, almost identical results will be found with the compounds wherein the phenyl rings contain other substituents. Among the most outstanding biocides of this series are those compounds of formula I wherein Y is alkoxycarbonyl, and the phenoxy or phenylthio substituent is in the p-position.

In general, the above compounds are made by following the basic procedure of Example 1, using the appropriate phenol or thiophenol and chloronitrobenzene as starting materials for making the necessary diphenyl ether or thioether. These ethers of formula II are routinely prepared by condensing an appropriate Y'-substituted phenol or thiophenol with the appropriate Y-substituted 1-chloro-4-nitrobenzene or 1-bromo-4-nitrobenzene in the presence of an equimolar amount of a base in an alcohol, DMF, DMSO or other known inert solvents or mixtures thereof. The nitro group of the obtained ether is then reduced to the corresponding primary amino group. Similarly, where Y or Y' is —COOH, corresponding alkoxycarbonyl substituents are used initially, followed by saponification after the nitro group is reduced. The preparation of these ethers or thioethers present no difficulty to the skilled artisan.

What is claimed is:

1. A compound of the formula

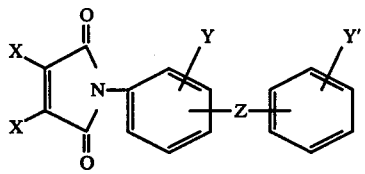

wherein substituents X both are either hydrogen or chlorine, Y represents 0-1 and Y' represents 0-2 substituents taken from the group consisting of halogen, trifluoromethyl, alkoxy with 1-4 carbon atoms, nitro, carboxy and loweralkoxycarbonyl, and Z is O or S, with the proviso that when Z is O, at least one substituent Y or Y' must be present.

2. A compound of the formula

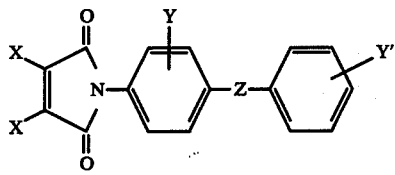

wherein X is H or Cl, Y is H or Cl, Y' is H, NO₂, Cl or 2 chlorines and Z is O or S, with the proviso that where Z is O, either Y or Y' is different from hydrogen.

3. The compound of claim 1 wherein each X is Cl, Z is O, Y is H and Y' represents NO₂, Cl or 2 chlorines.

4. The compound of claim 3, N-[p-(2,4-dichlorophenoxy) phenyl]maleimide.

5. The compound of claim 2, N-[p-(2,4-dichlorophenoxy)-2-methoxycarbonylphenyl]maleimide.

6. The compound of claim 2, N-[p-(4-nitrophenylthio)phenyl]-2,3-dichloromaleimide.

7. The compound of claim 2 N-[p-(4-nitrophenylthio)phenyl]maleimide.

8. The compound of claim 2, N-(p-phenylthiophenyl)maleimide.

9. The method of protecting a cellulosic, plastic or film-forming polymeric composition, knitted, woven, molded or extruded into a continuous form, against bacterial or fungal attack upon exposure to an environment containing common bacteria and fungi, comprising incorporating into said continuous form or coating said composition with a biocidally effective amount of a maleimide of the formula

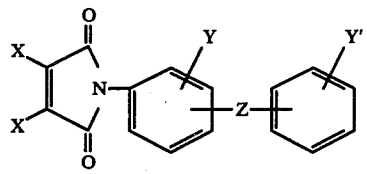

wherein both substituents X are either hydrogen or chlorine, Y represents 0-2 and Y' represents 0-2 substituents taken from the group consisting of halogen, trifluoromethyl, alkoxy with 1-4 carbon atoms, nitro, carboxy and loweralkoxycarbonyl, and Z is O or S, with the proviso that when Z is O, at least one substituent Y or Y' must be present.

10. The process of claim 9, wherein said biocidally effective amount is between 0.005 and 5.0% by weight.

11. The process of claim 9 wherein said maleimide is N-[p-(2,4-dichlorophenoxy)-2-methoxycarbonylphenyl]maleimide.

12. The process of claim 9 wherein said maleimide is N-[p-(2,4-dichlorophenoxy)phenyl]maleimide.

13. The process of claim 9 wherein said maleimide is N-[p-(4-nitrophenylthio)phenyl]-2,3-dichloromaleimide.

14. The process of claim 9 wherein said maleimide is N-[p-(4-nitrophenylthio)phenyl]maleimide.

15. The process of claim 9 wherein said maleimide is N-(p-phenylthiophenyl)maleimide.

* * * * *